(12) United States Patent
McKay

(10) Patent No.: US 6,270,528 B1
(45) Date of Patent: Aug. 7, 2001

(54) COMPOSITED INTERVERTEBRAL BONE SPACERS

(75) Inventor: William F. McKay, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/369,975

(22) Filed: Aug. 6, 1999

Related U.S. Application Data
(60) Provisional application No. 60/095,531, filed on Aug. 6, 1998.

(51) Int. Cl.⁷ .................................................. A61F 2/44
(52) U.S. Cl. .................................. 623/17.11; 623/16.11; 623/17.16; 623/17.12
(58) Field of Search .......................... 623/16.11, 17.11, 623/17.12, 17.16, 18.11, 23.62, 23.63

(56) References Cited

U.S. PATENT DOCUMENTS

| | | | |
|---|---|---|---|
| 4,294,753 | 10/1981 | Urist | 260/112 R |
| 4,627,853 | 12/1986 | Campbell et al. | 623/16 |
| 4,877,020 | 10/1989 | Vich | 128/92 |
| 4,877,864 | 10/1989 | Wang et al. | 530/324 |
| 4,950,296 | * 8/1990 | McIntrye | 623/16.11 |
| 5,013,649 | 5/1991 | Wang et al. | 435/69.1 |
| 5,053,049 | 10/1991 | Campbell | 623/16 |
| 5,106,748 | 4/1992 | Wozney et al. | 435/252.3 |
| 5,108,922 | 4/1992 | Wang et al. | 435/240.2 |
| 5,112,354 | 5/1992 | Sires | 623/16 |
| 5,116,738 | 5/1992 | Wang et al. | 435/69.1 |
| 5,171,279 | 12/1992 | Mathews | 623/17 |
| 5,187,076 | 2/1993 | Wozney et al. | 435/69.1 |
| 5,192,327 | 3/1993 | Brantigan | 623/17 |
| 5,306,303 | 4/1994 | Lynch | 623/16 |
| 5,366,875 | 11/1994 | Wozney et al. | 435/69.1 |
| 5,709,683 | 1/1998 | Bagby | 606/61 |
| 5,814,084 | 9/1998 | Grivas et al. | 623/16 |
| 6,022,376 | * 2/2000 | Assell et al. | 623/17.11 |
| 6,033,438 | 3/2000 | Bianchi et al. | 623/17 |
| 6,123,731 | * 9/2000 | Boyce et al. | 623/23.63 |
| 6,143,033 | * 11/2000 | Paul et al. | 623/17.11 |

FOREIGN PATENT DOCUMENTS

| | | | |
|---|---|---|---|
| WO 93/00432 | 1/1993 | (WO) . | |
| WO 94/26892 | 11/1994 | (WO) . | |
| WO 94/26893 | 11/1994 | (WO) . | |
| WO 97/25945 | 7/1997 | (WO) . | |
| WO 98/17209 | 4/1998 | (WO) . | |
| WO 98/17330 | 4/1998 | (WO) . | |
| WO 98/55052 | * 12/1998 | (WO) | 623/16.11 |

OTHER PUBLICATIONS

K.–U. Lewandrowski, W.W. Tomford, K.T. Schomacker, T.F. Deutsch, H.J. Mankin, "Improved Osteoinduction Of Cortical Bone Allografts: A Study Of The Effects Of Laser Perforation And Partial Demineralization", *J. Orthopaedic Research*, 15:748–756 (1997).

M.R. Urist, Y.K. Huo, A.G. Brownell, W.M. Hohl, J. Buyske, A. Lietze, P. Tempst, M. Hunkapiller, R.J. DeLange, "Purification Of Bovine Bone Morphogenetic Protein By Hydroxyapatite Chromatography", *Proc. Natl. Acad. Sci. USA*, 81:371–375 (Jan. 1984).

* cited by examiner

Primary Examiner—Pedro Philogene
(74) Attorney, Agent, or Firm—Woodard, Emhardt, Naughton, Moriarty & McNett

(57) ABSTRACT

Described are intervertebral spacer assemblies having reinforcing members or space-filling members. Also described are methods for fabricating intervertebral spacers, as well as methods for fusing adjacent vertebrae utilizing intervertebral spacers of the present invention.

17 Claims, 12 Drawing Sheets

COMPOSITED INTERVERTEBRAL BONE SPACERS

REFERENCE TO RELATED APPLICATION

The present application claims priority upon U.S. patent application Ser. No. 60/095,531, filed Aug. 6, 1998, which is hereby incorporated herein by reference in its entirety.

FIELD OF THE INVENTION

The present invention relates to intervertebral spacers. Specifically, the present composited intervertebral spacers including a first body of bone and a second body serving as in internal reinforcing member or as a complementary member to provide a uniform exterior surface to the spacer.

BACKGROUND OF THE INVENTION

As further background, numerous devices exist in the prior art to fill an intervertebral space following removal of all or part of the intervertebral disc in order to prevent disc space collapse and to promote fusion of the adjacent vertebrae within the disc space. Some of the earlier-developed devices stabilize the spinal column with a metal plate or rod spanning the affected vertebrae and fusion is promoted by disposing bone material between the adjacent vertebrae.

Several types of metal intervertebral spacers, including hollow spinal cages, are also currently being used to stabilize the spinal column. Fusion of adjacent vertebrae utilizing these spacers is typically promoted by filling the cages with an osteogenic material. Although metal plates, rods and spacers served the purpose of stabilizing the spinal column, the metallic devices remained as a permanent foreign body after fusion occurs. Attempts at alleviating this problem have included utilizing devices composed entirely of bone or having minimal metallic components.

Besides becoming incorporated into the resultant fusion mass, intervertebral spacers composed entirely of bone or having minimal metallic components have other advantages. For example, bone allows excellent postoperative imaging because it does not cause scattering like metallic spacers. Stress shielding is avoided because bone grafts have a similar modulus of elasticity as the surrounding bone. However, many of these bone spacers do not have sufficient compressive strength to withstand the cyclic loads of the spine, and the supply of suitable bone starting materials for fabrication of the spacers is limited in several respects. Needs thus exist for additional strategies for fabricating spacers possessing sufficient compressive strength to withstand the compressive loads of the spinal column and which provide flexibility in the use of existing bone stocks. The present invention address these needs.

SUMMARY OF THE INVENTION

Accordingly, in one preferred aspect, the present invention provides composited intervertebral spacers including a body of bone having a first end, a second end, a longitudinal axis and a channel extending therethrough parallel to the longitudinal axis. The channel is typically formed at least partially from a medullary canal of a bone from which the body of bone has been harvested. The spacer has a reinforcing member comprised of cortical bone or a similar high-strength material, disposed in the channel. A thru-hole may extend through the spacer transverse to the longitudinal axis of the spacer, which can be advantageously filled with an osteogenic material.

In a preferred form, the invention provides an intervertebral spacer including a body of bone having a longitudinal axis and a channel extending therethrough parallel to the longitudinal axis. The body has a first compressive strength in a first direction parallel to the longitudinal axis. The body also has a second compressive strength in a second direction generally perpendicular to the first direction. The second compressive strength is less than the first compressive strength. The spacer includes the body and a reinforcing member, preferably comprised of bone, disposed in the channel of the body.

A further preferred aspect of the invention provides a composited spacer having two or more complementary components which together define a substantially uniform exterior surface. The preferred composited intervertebral spacer includes an elongated body of bone having a longitudinal axis and a circumferential surface having a channel or groove extending perpendicular to the longitudinal axis. A complementary member is disposed within the channel such that the spacer has a substantially uniform circumferential surface, e.g., in the shape of a cylinder.

In another aspect of the invention, a method of preparing a reinforced, composited intervertebral spacer is provided. The method includes providing a body of bone having a first end, a second end, a longitudinal axis and an internal channel extending therethrough parallel to the longitudinal axis. The channel is typically formed at least partially from a medullary canal. The method further includes fitting a reinforcing member in the channel.

In yet another aspect of the invention, a method of preparing a composited intervertebral spacer is provided including providing an elongated body of bone having a longitudinal axis and a circumferential surface having a channel extending perpendicular to said longitudinal axis. The channel is formed at least partially from a medullary canal. The method includes fitting a complementary member in the channel and providing a uniform circumferential surface to the spacer. In this regard, the complementary member can be pre-shaped to provide the uniform surface upon insertion, or the complementary member can be shaped after insertion to provide the uniform surface.

A method of fusing adjacent vertebrae utilizing the intervertebral spacers described above is also described. The method includes providing a spacer as described above, preparing adjacent vertebrae to receive the spacer in an intervertebral space between adjacent vertebrae, and placing the spacer into the intervertebral space.

It is therefore an object of the invention to provide intervertebral spacers reinforced to provide sufficient strength to be used in intervertebral fusion procedures.

It is yet a further object of the invention to provide composited intervertebral spacers including a body and a complementary member which provides a desired uniform exterior surface.

It is yet a further object of the invention to provide methods for fabricating composited intervertebral spacers.

It is another object of the invention to provide methods for fusing adjacent vertebrae utilizing intervertebral spacers of the present invention.

These and other objects and advantages of the invention will become apparent after reading the following detailed description of preferred embodiment.

DETAILED DESCRIPTION OF THE PREFERRED EMBODIMENTS

For the purpose of promoting an understanding of the principles of the invention, reference will now be made to preferred embodiments thereof and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to intervertebral spacers comprised of bone and having advantageous biomechanical and physical properties. In certain embodiments of the invention, reinforced intervertebral spacers are provided having a natural channel (e.g., a medullary canal) running therethrough, that are obtained by making a cross-sectional cut in a bone. The compressive strength of the spacers is enhanced by disposing a reinforcing member, such as a cortical bone plug, in the channel. In another aspect of the invention, a composite spacer having a body with a natural channel running therethrough is provided. The channel is filled with a complementary member to form a spacer having a uniform exterior surface.

Figure 1:
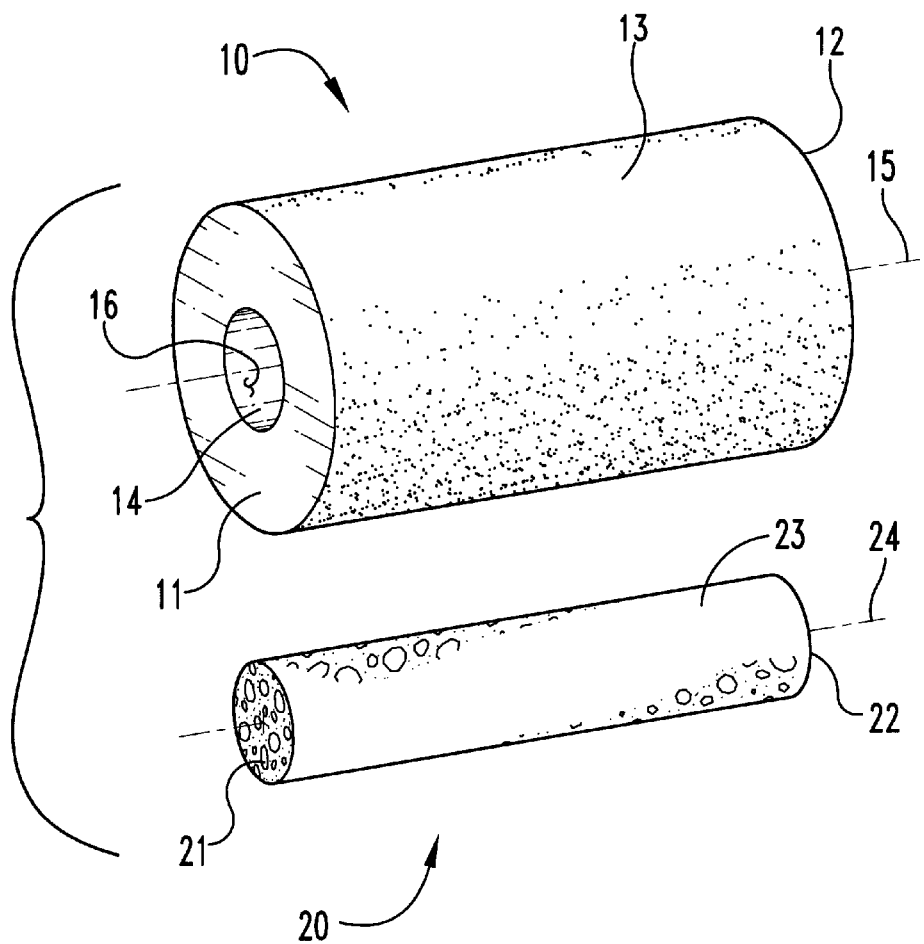
FIG. 1 shows a perspective view of one embodiment of the intervertebral spacer of the present invention, including a body of bone and a reinforcing member.

Referring now to FIG. 1, shown is a body of bone 10, such as a bone dowel, having a first end 11, a second end 12, an outer surface 13, a channel 14 extending through the body and a longitudinal axis 15. Body 10 is preferably substantially cylindrical. Moreover, channel 14 is defined by an inner surface of bone 16, is parallel to longitudinal axis 15 and is preferably formed at least partially from a natural channel, typically an inter-medullary canal. In this regard, channel 14, when formed at least partially from the inter-medullary canal, can for example be enlarged in diameter relative to the inter-medullary canal, lengthened in relation to the medullary canal, or both. For instance, the medullary canal may be shaped to ensure the canal has a shape that corresponds to the exterior profile presented by a reinforcing member (discussed below) by methods known in the art, including reaming, drilling (including use of a tapered drill) or the like. In addition, the substantially cylindrical exterior surface may be provided by the natural shape of the source bone, or the exterior surface of the source bone may be machined to provide a cylindrical or other-shaped surface, and/or surface features such as grooves or threads to resist expulsion from an intervertebral space, as desired.

Body 10 is preferably comprised of cortical bone. The source of the cortical bone advantageously includes the fibula, radius, ulna, small humeri, femur, tibia or humerus. In general, when the spacer is to be used as a cervical intervertebral spacer, it is preferred to obtain the body from smaller bones, including the fibula, radius, ulna or humerus. When the spacer is to be incorporated into lumbar or thoracic intervertebral spaces, body 10 is preferably obtained from larger bones, including, for example, the femur, tibia and humerus. The source bone is obtained from an acceptable donor based upon appropriate standards for the particular donor and recipient. In this regard, the source bone can be allographic or xenographic with respect to the recipient of the spacer.

For human bone, to be used for instance as an allograft in a human recipient, some form of consent such as a donor card or written consent from the next of kin is usually required for the human donor. When the recipient is human, the donor is usually screened for a wide variety of communicable diseases and pathogens, including human immunodeficiency virus, cytomegalovirus, hepatitis B, hepatitis C and several other pathogens. These tests may be conducted by any of a number of means conventional in the art, including, but not limited to, ELISA assays, PCR assays, or hemagglutination. Such testing follows the requirements of: (i) American Association of Tissue Banks, Technical Manual for Tissue Banking, Technical Manual—Musculoskeletal Tissues, pages M19–M20; (ii) The Food and Drug Administration, Interim Rule, Federal Register/Vol. 58, No. 238/Tuesday, Dec. 14, 1994/Rules and Regulations/65517, D. Infectious Disease Testing and Donor Screening; (iii) MMWR/Vol. 43/No. RR-8m Guidelines for Preventing Transmissions of Human Immunodeficiency Virus Through Transplantation of Human Tissue and Organs, pages 4–7; and (iv) Florida Administrative Weekly, Vol. 10, No. 34, Aug. 21, 1992, 59A-1.001-01459A-1.005(12)(c), F.A.C., (12)(a)–(h), 59A-1.005 (15), F.A.C., (4)(a)–(8).

In addition to a variety of standard biochemical assays, the donor, or their next of kin, is interviewed to determine whether the donor engaged in any of a number of high risk behaviors including having multiple sexual partners, suffering from hemophilia and engaging in intravenous drug use. Once a donor has been determined to be acceptable, the bones for obtaining the components of the spacers are recovered and cleaned.

For allographic bone sources or for xenographic bone sources, for example in the case of bovine bone to be used in a human recipient, the bone can be treated to reduce its immunogenicity to the recipient. For example, the bone may be calcined or treated to remove or modify non-collagenous proteins that may cause an immunogenic reaction in the recipient. Advantageously, such processed bone can thereafter be treated to incorporate an osteogenic factor such as a bone morphogenetic protein (e.g. BMP-2), to restore bone inductive properties to the bone.

Body 10 is preferably obtained as a longitudinal segment of the source bone, e.g., by making cross-sectional cuts in the source bone described above. Although not necessary to the broader aspects of the invention, the source bone typically can withstand a greater compressive load in a direction along planes parallel to the longitudinal axis of the source bone as compared to a direction along planes perpendicular to the longitudinal axis of the source bone. Therefore, body 10, obtained as a longitudinal segment of the source bone, will have a greater compressive strength in a first direction along planes parallel to longitudinal axis 15 of body 10. However, body 10 is configured to be placed into an intervertebral space such that the predominant compressive load of the spine will be in a second direction along planes substantially perpendicular to the first direction. As such, in accordance with the present invention, the structural integrity of body 10 is increased by disposing a reinforcing member 20, also depicted in FIG. 1, in channel 14 of body 10. The reinforcing member will preferably have a compressive strength in a direction perpendicular to its longitudinal axis at least equal to or greater than that of the body 1, and may be locked in place with a press fit or Morris taper fit and/or by use of adhesives or similar bonding materials known in the art.

Figure 2:
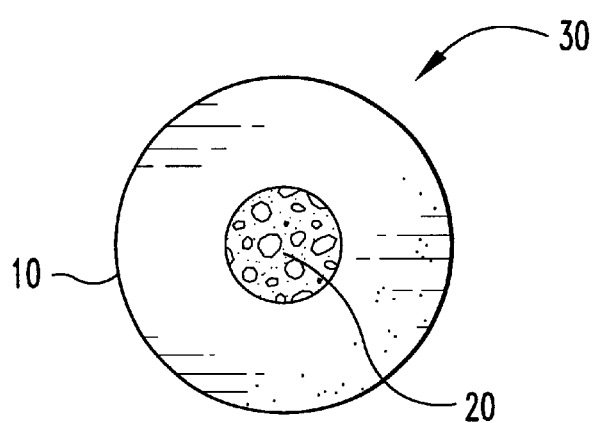
FIG. 2 shows an end view of the intervertebral spacer formed by disposing the reinforcing member of FIG. 1 into the channel of the body of bone of FIG. 1.

FIG. 1 further shows that reinforcing member 20 has a first end 21, a second end 22, an outer surface 23 and a longitudinal axis 24. The length and diameter of reinforcing member 20 may vary but the member is preferably of a length that will substantially fill the channel. For example, reinforcing member 20 may have a diameter such that outer surface 23 along the length of body 10 will be in contact with inner surface 16 of channel 14. Reinforcing member 20, when inserted in body 10 of FIG. 1, typically extends from first end 11 to second end 12 of the body. However, reinforcing member 20 may include multiple reinforcing members, such as two, wherein each member may be placed in a line within the channel at a different point along the length of body 10 such that at least one end of each member faces an end of another member. Reinforcing member 20 may be comprised of a metal, metal alloy, ceramic, bone cement (e.g. polymethylmethacrylate-based cement), synthetic polymer such as polyethylene (including biodegradable polymers) or any other material of sufficient compressive strength to withstand the compressive load of the spine when the member is disposed within channel 15. However, reinforcing member 20 is preferably comprised of bone, such as a bone dowel or bone plug, and most preferably comprised of cortical bone. The bone may be from a femur, humerus, tibia, fibula, radius, ulna or small humeri. FIG. 2 shows reinforcing member 20 disposed in channel 14 of body 10 to form spacer 30.

Reinforcing member 20 has sufficient compressive strength to provide an overall spacer having increased structural integrity as compared to body 10 alone. As a preferred example, reinforcing member 20 is desirably composed of cortical bone, and can be obtained by making a transverse cut or bore through the source bone such that a member of uniform circumference is obtained. A reinforcing member obtained in such a fashion will be able to withstand a greater compressive load in a direction along planes perpendicular to longitudinal axis 24 of reinforcing member 20, as this direction is along planes parallel to the longitudinal axis of the source bone. Moreover, it is preferable to obtain a reinforcing member that is solid, i.e., one with no internal channels.

Reinforcing member 20 may also be comprised of a suitable bone cement which has been disposed within the channel 14 of body 10, and caused to harden to a solid mass filling the channel 14. Suitable bone cements are known in the art and include, for example, polymethylmethacrylate cements and calcium phosphate cements. When using a bone-cement reinforcing member 20, channel 14 of body 10 can be reamed or machined to provide uniformity as compared to its natural state. Advantageously, however, channel 14 need not be so reamed or machined due to the flow properties of the cement prior to hardening which allow it to fill even irregularly shaped channels 14.

Figure 3A:
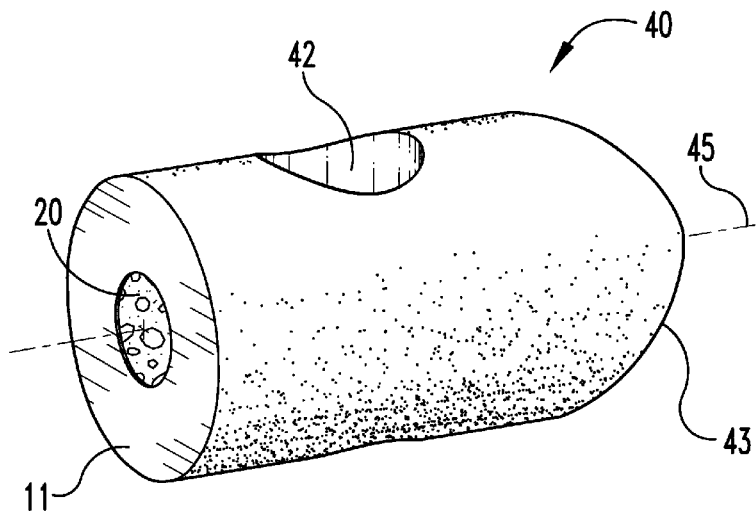
FIG. 3A shows a perspective view of the intervertebral spacer of FIG. 2 with a chamfered end and a thru-hole.

In one aspect of the invention, at least one thru-hole is provided in the body of the spacer. Referring to FIG. 3A, it is seen that thru-hole 42 extends through spacer 40 and is transverse to longitudinal axis 45. Thru-hole 42 may be formed by various methods as known in the art, including, for instance, machining methods such as drilling. Thru-hole 42 is advantageously filled with an osteogenic material. In one aspect of the present invention, the spacer may have a chamfered end presenting a curvature that facilitates insertion of the spacer into the intervertebral space. The spacer of FIG. 3A also has a chamfered second end 43 that is the first end to be inserted into an intervertebral space. Chamfering can be accomplished by appropriate means known in the art such as by machining, filing, sanding or other abrasive means. The tolerance for the chamfering is liberal and the desired object is to round or slightly point an end of the spacer that is to be inserted into the intervertebral space.

Figure 3B:
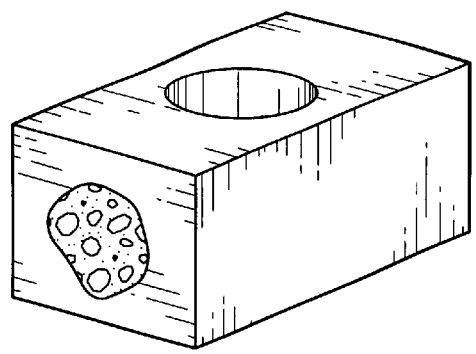
FIGS. 3B–D show perspective views of flat intervertebral spacers of the invention.
Figure 3C:
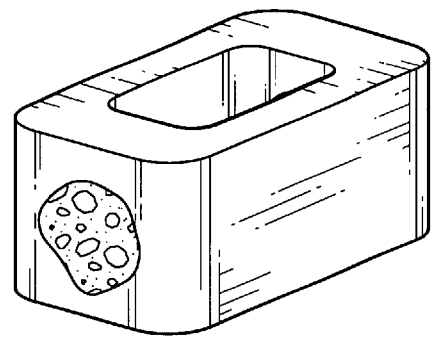
Figure 3D:
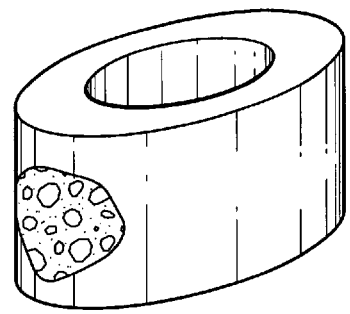
Figure 6:
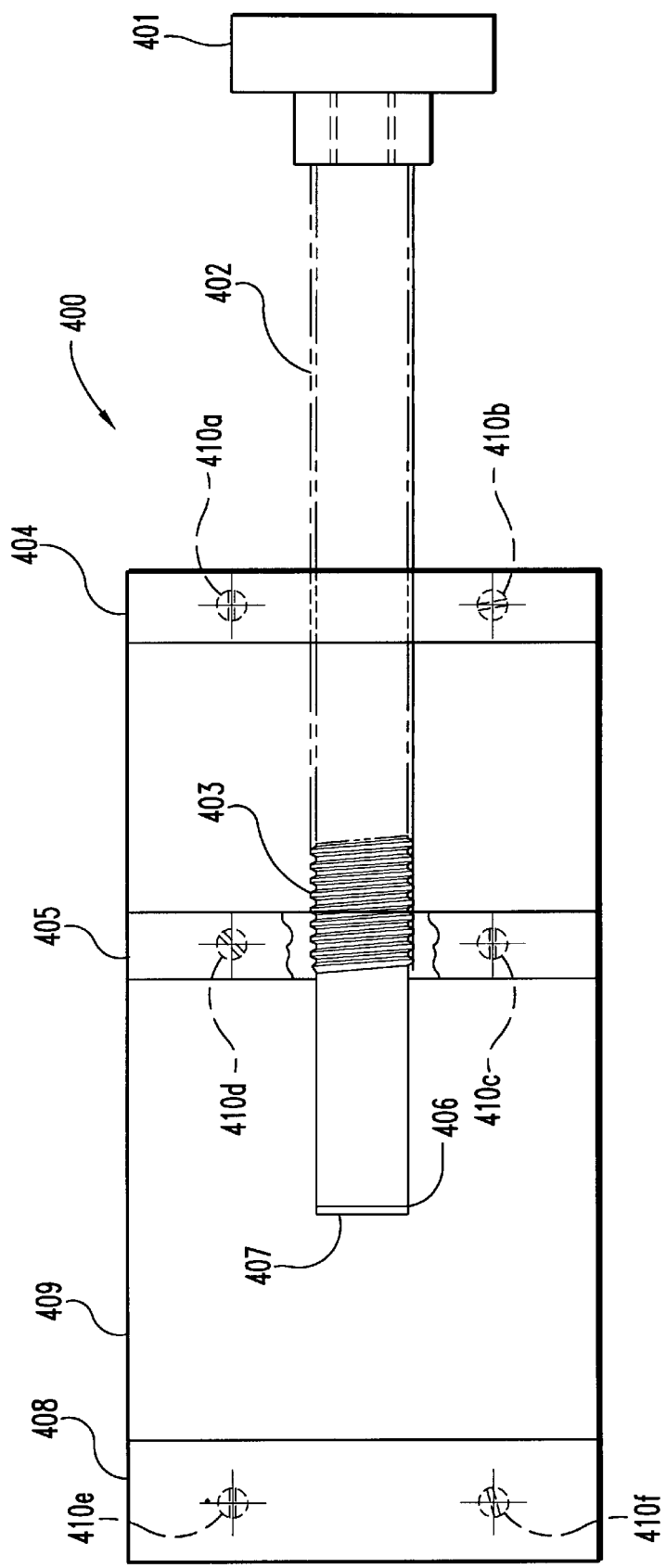
FIG. 6 is a top elevational view of one embodiment of a dowel threader.

Referring now to FIGS. 3B–D, shown are additional intervertebral spacers in accordance with the invention, which can be machined from source bones having had their natural channels filled with bone, bone cement or other reinforcing members as discussed herein. The spacers depicted in FIGS. 3B–D are "flat" spacers in that they have generally flat upper and lower surfaces for contacting the vertebrae between which they are disposed. Such spacers may be used, for instance, in Smith-Robinson type fuisions. In particular, FIG. 3B depicts a flat spacer having a box shape, a thru-hole and squared exterior corners, FIG. 3C depicts a flat spacer having a box shape, a thru-hole and rounded exterior corners, and FIG. 3D depicts a flat spacer having a generally ovoid shape and a thru-hole. Machining to provide these and other usefull spacer shapes will be within the purview of those of ordinary skill in the art.

Any suitable osteogenic material or composition can be used to fill the thru-hole(s) of spacers of the invention, including for example autogratt, allograft, xenograft, demineralized bone, synthetic and natural bone graft substitutes, such as bioceramics and polymers, and osteoinductive factors. Autograft can be harvested from locations such as the iliac crest using drills, gouges, curettes and trephines and other tools and methods which are well known to surgeons in this field. Preferably, autograft is harvested from the iliac crest with minimally invasive surgery. The osteogenic material may also include bone reamed away by the surgeon while preparing the end plates for the spacer.

Advantageously, where autograft is chosen as the osteogenic material, only a very small amount of bone material is needed to pack the thru-hole. The autograft itself is not required to provide structural support as this is provided by the spacer. The surgery for such a small amount of bone is less invasive and better tolerated by the patient. There is usually little need for muscle dissection in obtaining such small amounts of bone. The present invention therefore eliminates or minimizes many of the disadvantages of employing autograft in relatively larger quantities.

Natural and synthetic graft substitutes which replace the structure or function of bone are also contemplated for use as the osteogenic composition. For example, these may include demineralized bone matrix, mineral compositions and bioceramics. There is a vast array of bioceramic materials, including BIOGLASS®, hydroxyapatite and calcium phosphate compositions known in the art which can be used to advantage for this purpose. For additional information as to such compositions, reference can be made to *An Introduction to Bioceramics*, edited by Larry L. Hench and June Wilson (World Scientific Publishing Co. Ptd. Ltd., 1993, volume 1), the disclosure of which is herein incorporated by reference.

In some embodiments, the osteogenic compositions used in this invention comprise an effective amount of a substantially pure bone inductive factor, or growth factor to stimulate or induce bone growth, including factors comprised of protein or genes. Recombinant human bone morphogenetic proteins (rhBMPs) are preferred. Most preferably, the bone morphogenetic protein is a rhBMP-2, rhBMP-4 or heterodimers thereof.

Recombinant BMP-2 can be used at a concentration of about 0.4 mg/ml to about 4.0 mg/ml, preferably about 1.0 to 3.0 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371, 1984.

The choice of carrier material for the osteogenic composition is based on biocompatibility, biodegradability, mechanical properties and interface properties as well as the structure of the spacer that will act as a load bearing member. The particular application of the compositions of the invention will define the appropriate formulation. Potential carriers include calcium sulfates, polylactic acids, polyanhydrides, collagen, calcium phosphates, polymeric acrylic esters and demineralized bone. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is a biphasic calcium phosphate ceramic. Ceramic blocks are commercially available from Sofamor Danek Group, GmbH of Deggendorf, Germany and Bioland, 132 Rou d Espangne, 31100 Toulouse, France. The osteoinductive material can be introduced into the carrier in any suitable manner. For example, the carrier may be soaked in a solution containing the factor.

The intervertebral spacer of the present invention may also have surface features, including grooves and threads, on the outer surface of the spacer. The grooves and/or threads may be introduced to the outer surface of the spacer before or after the thru-holes discussed above are formed. Both threads and grooves serve a surface-engaging function. The threads, in particular, allow better control of spacer insertion compared to smooth spacers. The surgeon can thus more accurately position the spacer and avoid over-insertion which is extremely important around the critical neurological and vascular structures of the spinal column. Additionally, threads and grooves provide increased surface area which facilitates the process of bone healing and creeping substitution for replacement of the donor bone material and fusion. The threads and grooves also stabilize the bone-spacer interface, reduce micromotion to facilitate incorporation and fusion and help prevent expulsion of the spacer from the intervertebral space.

Figure 4:
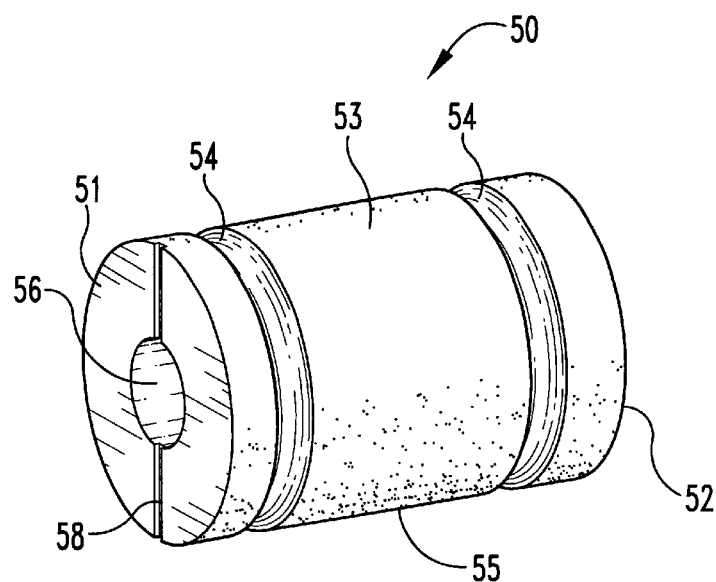
FIG. 4 shows a perspective view of the intervertebral spacer depicted in FIG. 2 with grooves on its outer surface.

As an illustration, referring to FIG. 4, outer surface 53 of body 55 of spacer 50 defines grooves 54. Grooves 54 are preferably adjacent to respective first end 51 and second end 52. An alignment score mark 58 can be seen at first end 51, which in this embodiment defines a tool engaging end. The score mark may be widened to form a driver slot for receiving an implantation tool. Alternatively, the end of the spacer may be machined to exhibit a projection instead of a slot. Such a protruding portion of bone may have a straight, flat-sided shape, or may be an elliptical eminence, a bi-concave eminence, a square eminence or any other protruding shape which provides sufficient end-cap or tool engaging end strength and drive purchase to allow transmission of insertional torque without breaking the spacer or the eminence. In other embodiments, a groove can be omitted to enhance the strength of first end 51. It is also seen in FIG. 4 that first end 51 further defines an instrument attachment hole 56.

Figure 5:
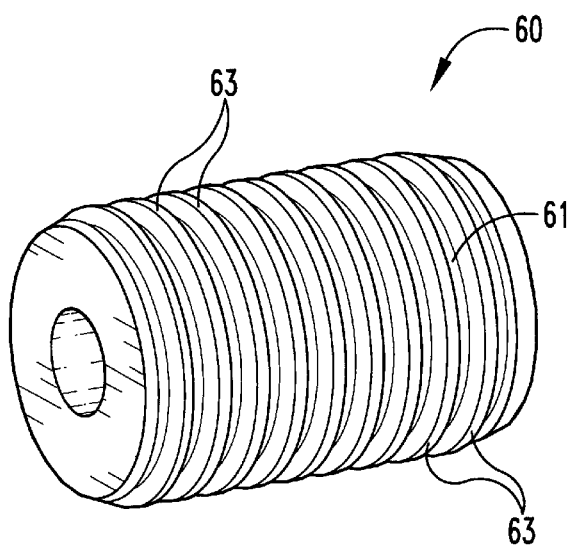
FIG. 5 shows a perspective view of the intervertebral spacer of FIG. 2 with threads on its outer surface.

Referring to FIG. 5, an intervertebral spacer 60 having threads 63 on outer surface 61 of spacer 60 is shown. As discussed above, the threads provide engaging surfaces to facilitate engagement with the vertebrae and prevent slippage of the spacer.

Figure 7:
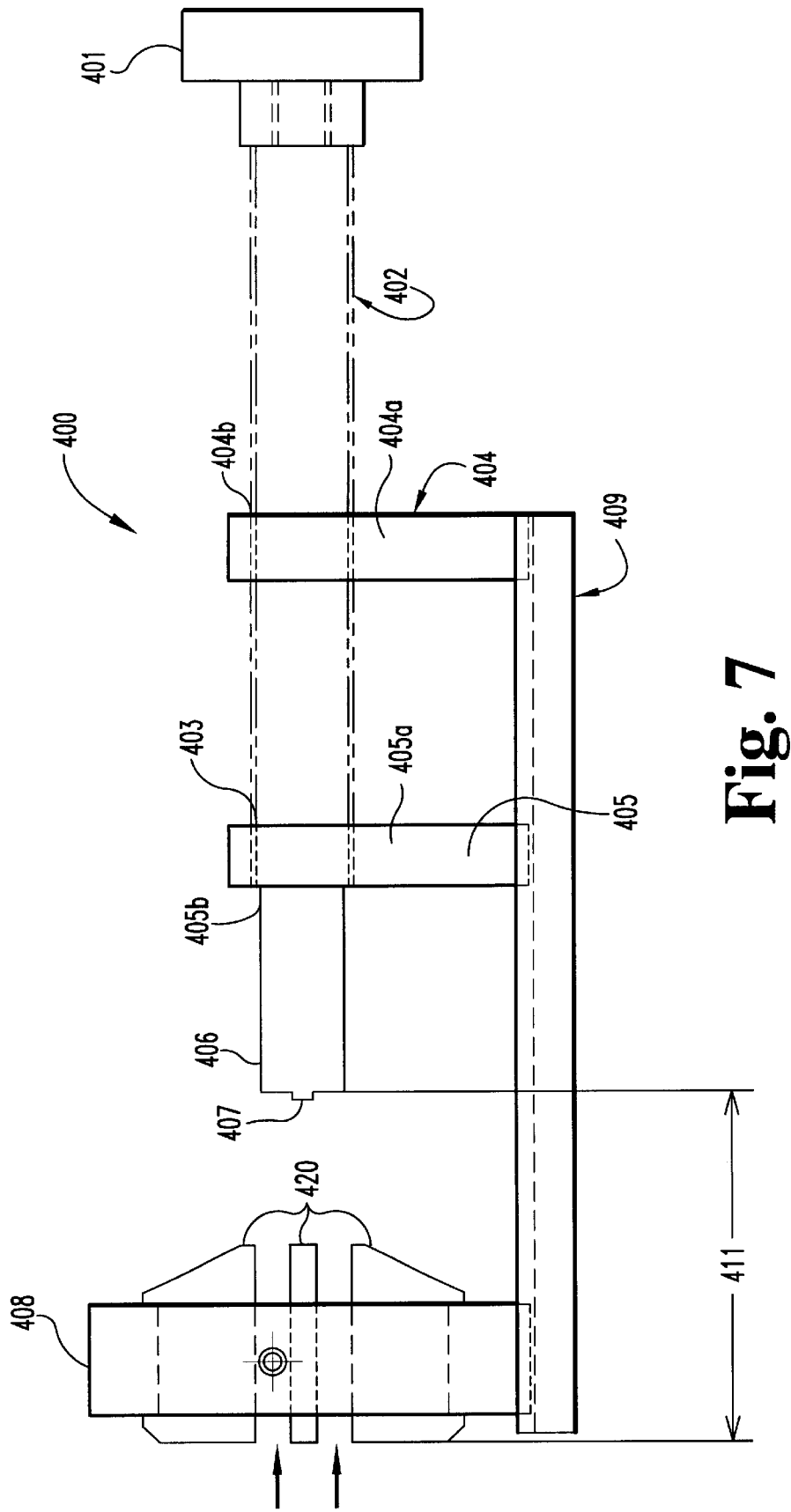
FIG. 7 is a side elevational view of the dowel threader of FIG. 6.
Figure 8:
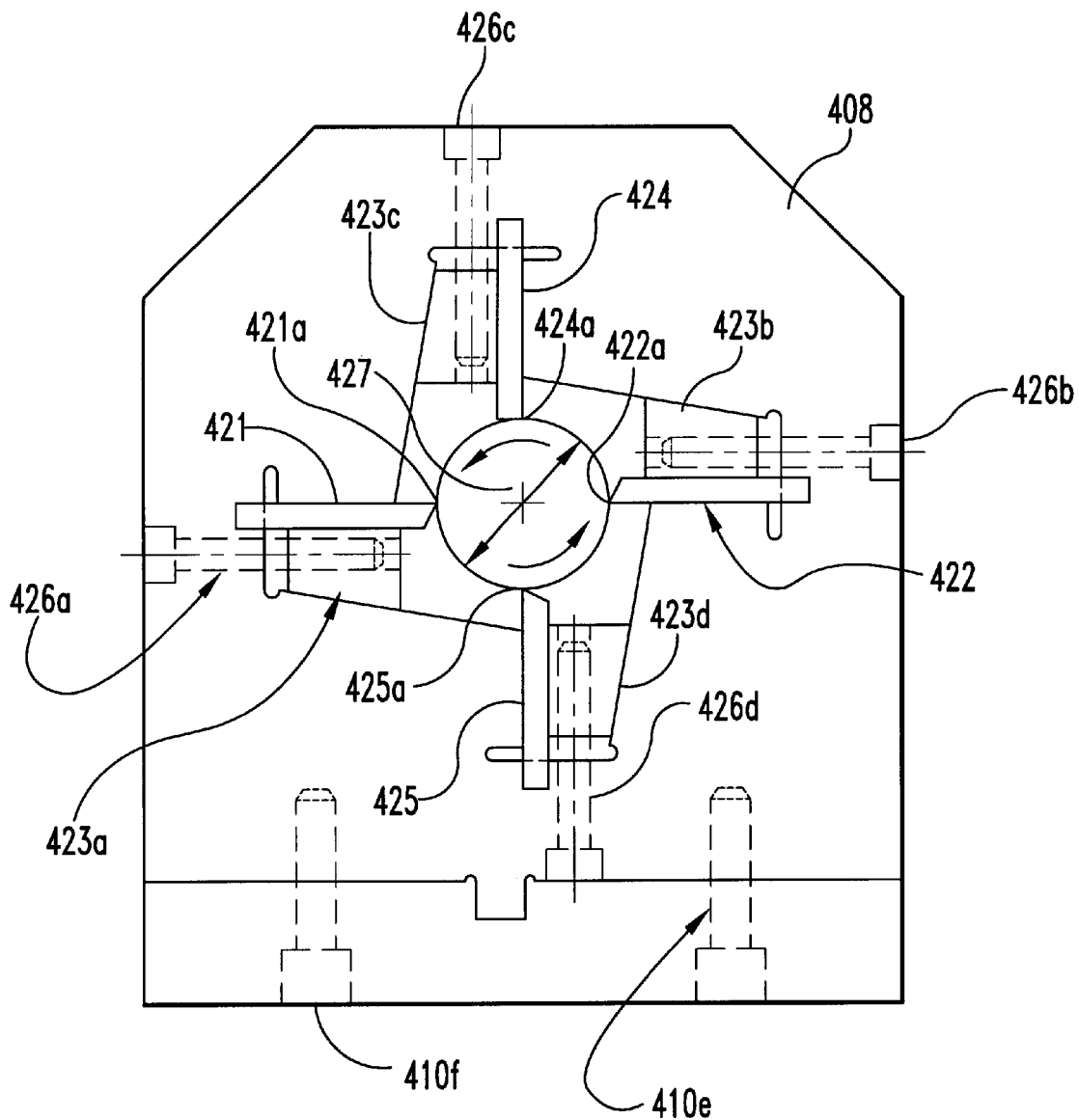
FIG. 8 is an end elevational view of the dowel threader of FIGS. 6 and 7 showing elements of the cutter assembly.

A number of different methods exist as known by those skilled in the art to provide the threaded or grooved embodiments of the spacer referred to in FIGS. 4 and 5. One preferred method utilizes a thread cutter referred to in FIGS. 6–12. The cutter 400 includes a drive shaft 402 for supporting a spacer and a cutter assembly 420. The terminal end 406 of the drive shaft 402 includes a spacer engager 407. In one embodiment and as best shown in FIG. 7, the spacer engager 407 is a protruding element which matingly corresponds to the driver slot on the tool end of the open-chambered spacers of this invention. The drive shaft 402 can be turned to rotate and advance the spacer incrementally through the cutter assembly 420 to inscribe a feature such as a thread into the surface of the spacer.

In one embodiment, the drive shaft 402 can be turned by a handle 401 rigidly attached to a first end 402a of the shaft 402. The drive shaft 402 preferably is provided with a graduated segment means for controlled incremental advancement of the drive shaft 402 upon rotation of the handle 401. In this embodiment, the means is a threaded portion 403. Support means 404 and 405 are preferably provided for alignment and support of he shaft 402. Each of the support means 404 and 405 include a wall 404a and 405a, respectively, defining an aperture 404b and 405b, respectively. The support means 404 and 405 may have controlling means within the apertures 404b and 405b, respectively, for controlling rotation and incremental advancement of the shaft. In some embodiments, the controlling means include matching threads or bearings.

The thread cutter assembly includes a housing 408 and blades 421 and 422 and guide plates 424, 425 mounted within the housing 408. The cutter blades 421 and 422 are held in place in the housing 408 by fixation wedges 423a and 423b, respectively, while guide plates 424 and 425, having no cutting teeth, are held in place by fixation wedges 423c and 423d, respectively. Fixation wedges 423a–d are held in place by screws 426a–d. The foregoing arrangement is preferred, as it allows for easy assembly and disassembly of the cutter assembly, removal of the cutter blades, cleaning of the various components, and if desired, sterilization by autoclaving, chemical, irradiative, or similar means. The cutter blades 421 and 422 and guide plates 424 and 425 may be rigidly fixed in place by increasing the tension created by tightening screws 426a–d, which draws the fixation wedges 423a–d into the housing 408, thereby clamping these elements in place. Naturally, based on this disclosure, those skilled in the art will be able to develop equivalents of the cutter assembly system described herein, such as by use of wing-nuts, welding or like means to affix these various elements in appropriate cutting relationship to each other.

Fixation wings 421c and 421d are provided to allow proper seating of the cutter blade upon insertion into the housing 408. A line is provided at θ on cutter blades 421 and 422, which allows for appropriate registration between cutter blades 421 and 422 during manufacture thereof. Upon insertion into the housing 408, it is critical that the blades and the teeth thereon are appropriately registered so that as blade 421 cuts into the bone dowel as it is rotationally advanced through the cutter assembly 420, blade 422 is appropriately situated so that its matching teeth are in phase with the thread inscribed by the teeth on blade 421. This is accomplished by a combination of the fixation wings 421d and 421c properly seating in the housing 408 such that wall 421c abuts the housing 408 and the housing 408 walls abut the insides of wings 421d and 421c.

The cutting edges 421a and 422a of the blades 421 and 422, respectively, are disposed in relation to each other so that they are on axis. The cutting edges 421a and 422a and the guiding edges 424a and 425a of the guide plates define an aperture 427 for a spacer or dowel. The diameter of the dowel that may be threaded according to this device is defined by the diameter of the aperture 427.

The supports 404 and 405 and the housing 408 for the cutter assembly are all preferably mounted on a steady, solid, weighty base unit 409 via screws, welding, or similar attachment means at 410a–f. The supports and the cutter assembly are configured so that there is appropriate travel distance 411 from the fully backed out terminal end of the drive shaft 406 to the end of the cutter assembly 420. This distance must be sufficient to allow insertion of a dowel blank and advancement of the blank through the cutter assembly 420 to allow a fully threaded dowel to emerge from the cutter assembly.

Figure 9:
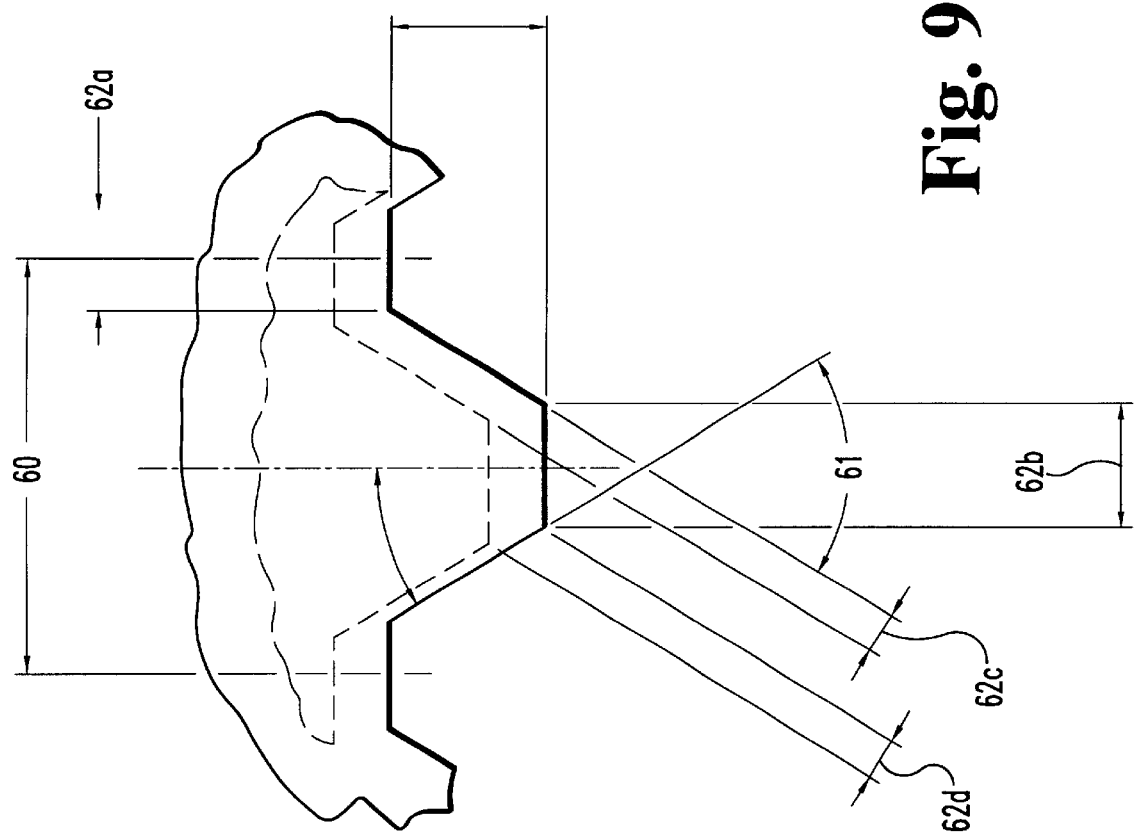
FIG. 9 is a detailed view of a single tooth of one cutter blade of the dowel threader.
Figure 10:
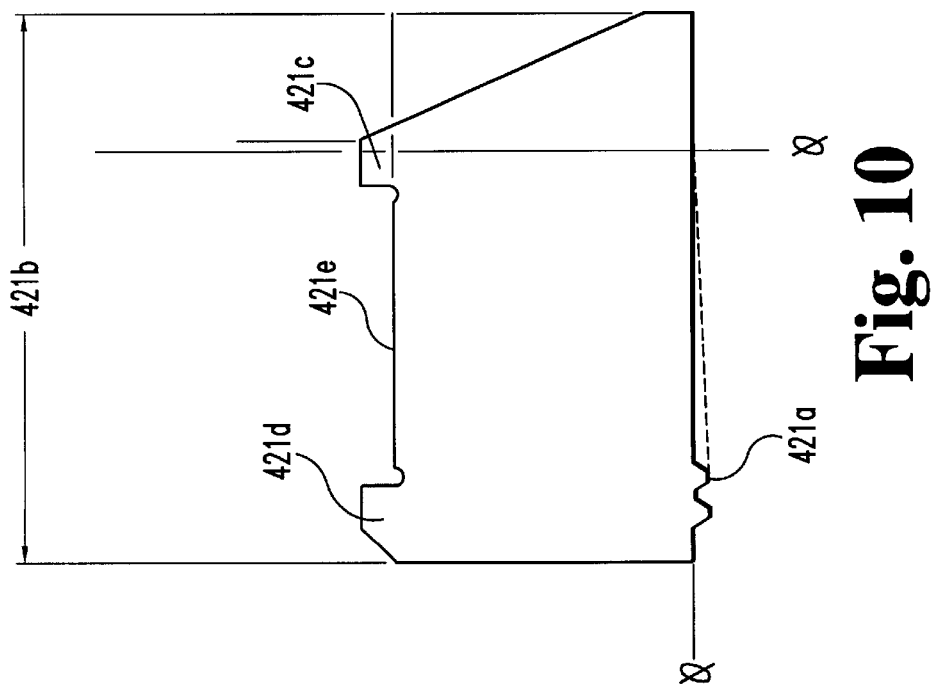
FIG. 10. is a global side view of a cutter blade.

The cutter maintains true tooth form from top to bottom, so that the cutter can be sharpened by surface grinding the face. This is achieved by wire-cutting the teeth such that there is about a 5° incline 62c between the descending vertices at the front and rear of each tooth, and about an 8° incline 62d between the front and rear of the top of each tooth. This aspect can best be seen in FIG. 9. Additionally, the thickness of the cutter blade, 62c, is preferably about 0.100 inches as seen in FIG. 9. The angle 61 in FIG. 9 is preferably about 60°. The width of the top of the tooth 62b is preferably about 0.025 inches. The pitch 60 is preferably about 0.100 inches. FIG. 10 shows an overall view of the cutter blades 421 or 422 which are assembled in the cutter assembly housing 408. The entire length of the cutter blade 421b is about 1.650 inches.

Figure 11:
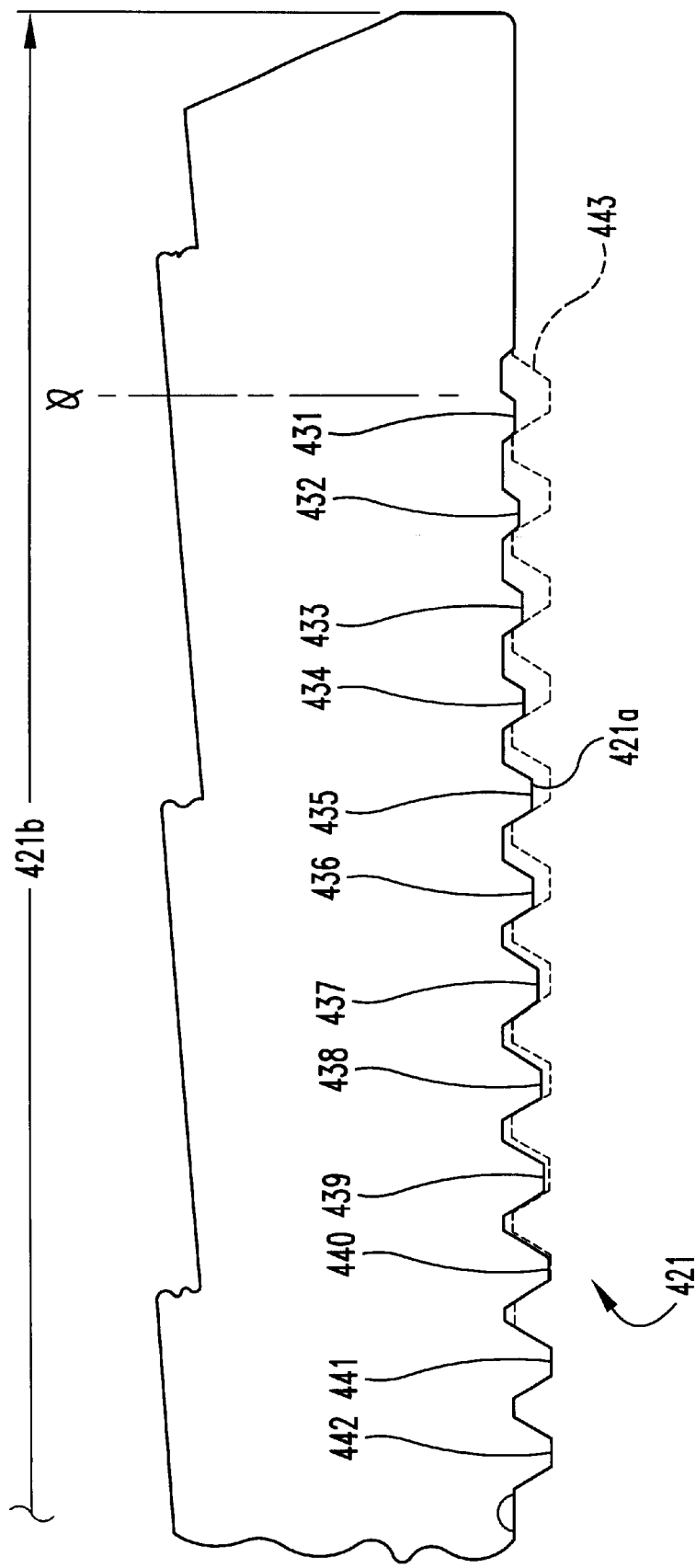
FIG. 11 is a detailed side view of the cutter blade of FIG. 10.
Figure 12:
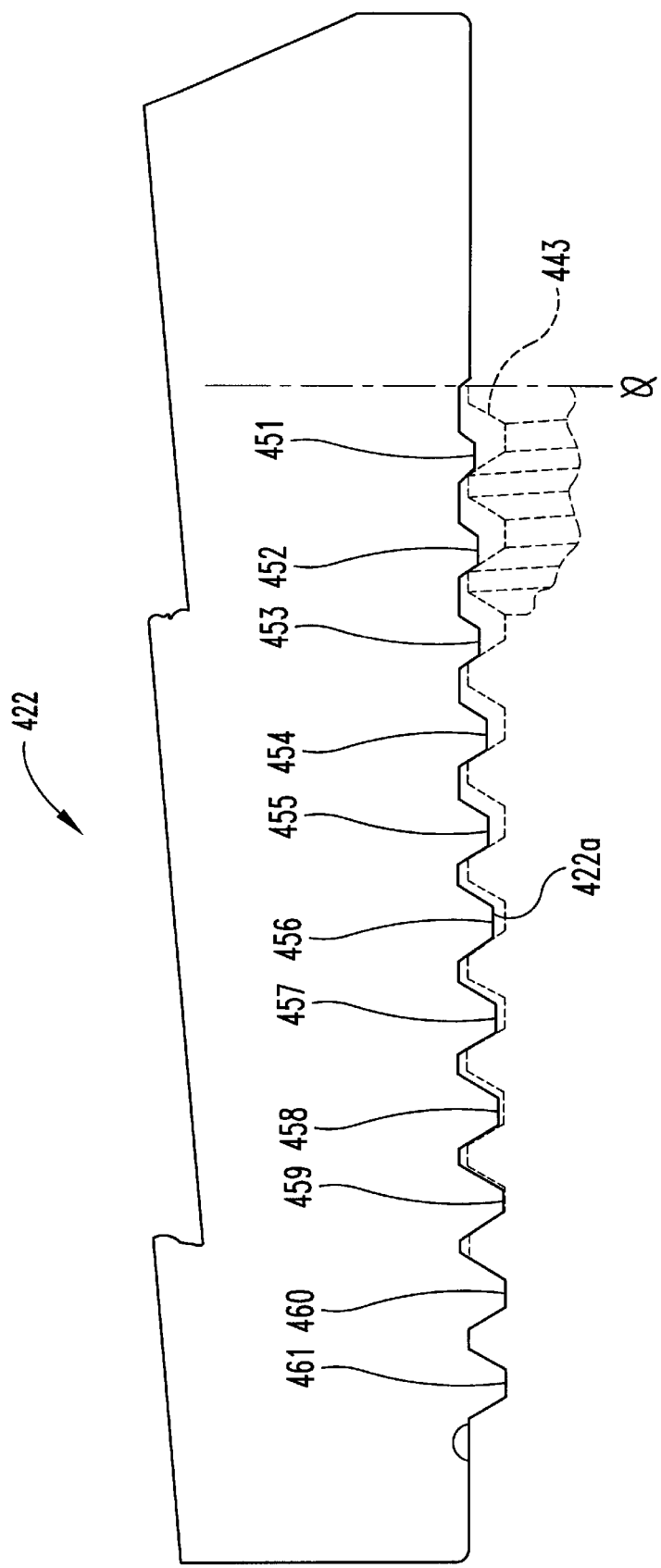
FIG. 12 is a detailed side view of the cutter blade of FIGS. 10 and 11.

Details of the blades 421 and 422 are shown in FIGS. 11 and 12. In this embodiment, the cutter blade 421 has twelve cutting teeth 431–442. The cutting edge 422a has eleven teeth 451–461 spread over the length of the blade 422. First tooth 451 at a height of 0.004 inches in this example is encountered by the blank and at each successive tooth, an increase of about 0.004 inches is made until the final tooth height of about 0.039 inches is reached at tooth 460 and 461. As a dowel blank is fed into the cutter assembly, it first encounters a truncated tooth at 431, and at every subsequent tooth, the height of the tooth is reached, in this example, of 0.039 inches at 441 and 442. The truncated teeth 431–440 feed into the dowel being cut along the 30° line so that the teeth cut on only two sides. The dotted line 443 shows the final pitch and form that the cutter will cut in the bone dowel.

It will be recognized by those skilled in the art that all of the foregoing elements should preferably be manufactured from durable materials such as stainless steel, or similar materials. In particular, the cutting surfaces 421a and 422a of the blades 421 and 422, respectively, are made from hard metal.

In operation, based on the foregoing description, it will be appreciated that the cutter blades 421 and 422 are placed into the housing 408, clamped into place via the fixation wedges 423a and 423b and the screws 426a and 426b after the blades have been properly seated and the two blades are perfectly aligned. A blank dowel is then loaded into the aperture 427 and the drive shaft with the protruding element 408 is inserted into a drive slot a dowel. As the handle 401 is turned, the drive shaft forces the dowel to rotate and advance incrementally through the cutter assembly 420, thereby inscribing the thread defined by the cutter blades 421 and 422 into the outer cylindrical surface or circumference of the dowel.

As noted above, those skilled in the art will recognize that modifications to the device described will allow for the preparation of the varied threads or grooves in the circumference of the dowel. For example, to form a groove in a dowel, the dowel could be mounted in a lathe, such as those known in the art and commercially available, for example, from SHERLINE PRODUCTS, INC., San Marcos, Calif. 92069, and a cutter blade applied as the dowel is rotated.

Figure 13:
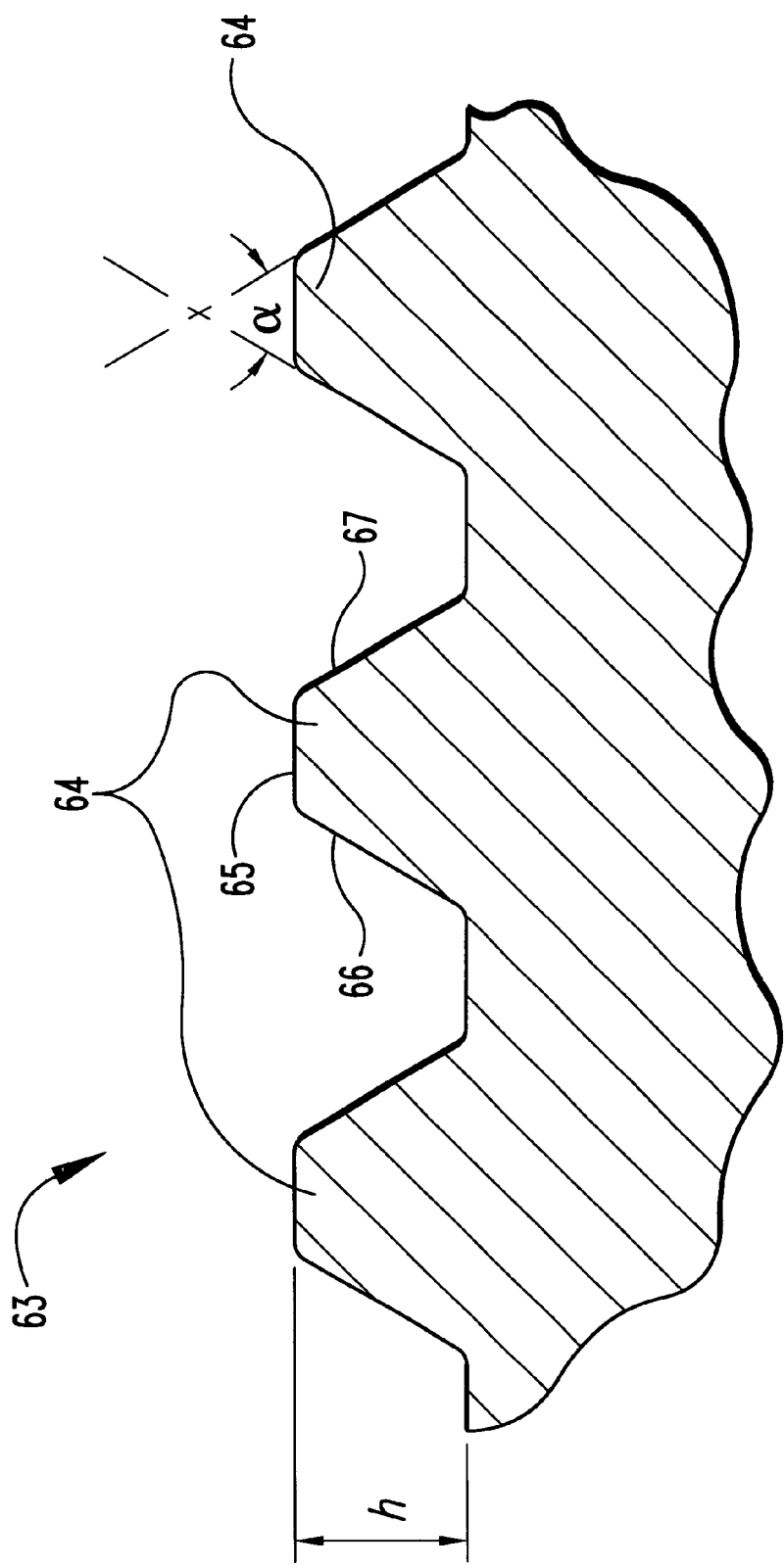
FIG. 13 is a side cross-sectional view of a portion of the threads of the intervertebral spacer of FIG. 5.

As seen in FIG. 13, threads 63 are preferably uniformly machined threads which include teeth 64 having a crest 65 between a leading flank 66 and an opposite trailing flank 67. Crest 65 of each tooth 64 is typically flat. In one specific embodiment, crest 65 of each tooth 64 has a width of about 0.020 inches to about 0.030 inches. Threads 63 preferably define an angle α between leading flank 66 and trailing flank 67. Angle α is typically about 50° to about 70°. Each tooth 64 preferably has a height "h" of about 0.030 inches to about 0.045 inches.

Figure 14:
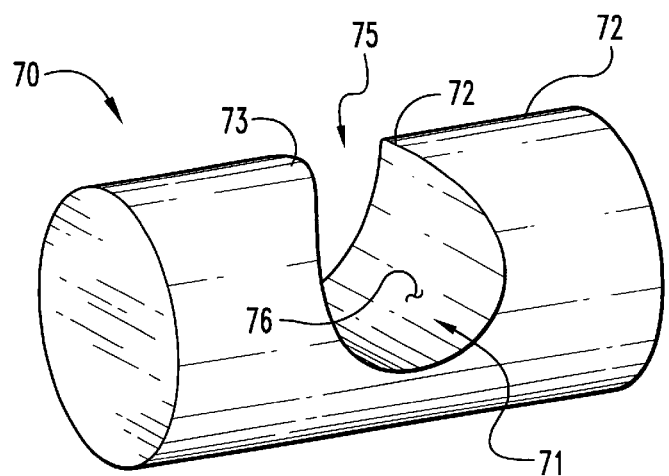
FIG. 14 shows a perspective view a C-shaped body that is incorporated into an intervertebral spacer of the present invention.
Figure 15:
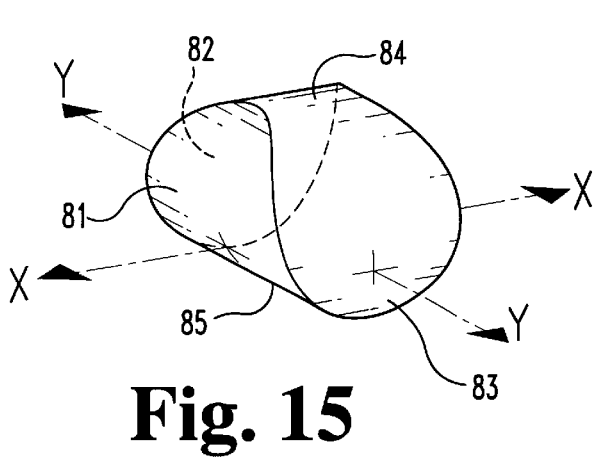
FIG. 15 is a perspective view of a complementary space-filling member that may be disposed in the C-shaped body of the intervertebral spacer depicted in FIG. 14 to form an alternative embodiment of the intervertebral spacer of the present invention.
Figure 15A:
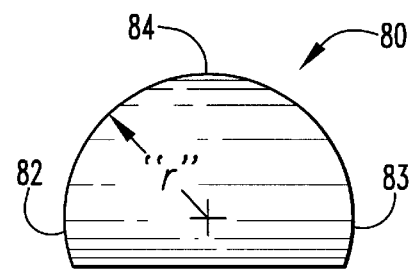
FIG. 15A is an end view of the complementary space-filling member depicted in FIG. 15.
Figure 17:
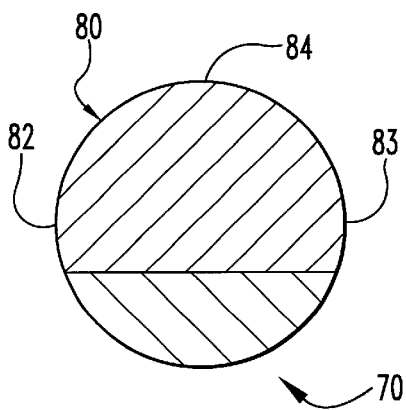
FIG. 17 is an end view of the intervertebral spacer of FIG. 16.
Figure 16:
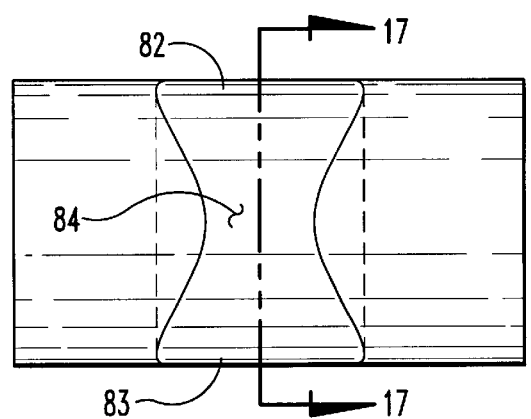
FIG. 16 is a top view of one embodiment of the intervertebral spacer of the present invention formed by disposing the complementary space-filling member of FIGS. 15 and 15A into the channel of the C-shaped body of FIG. 14.

The present invention also provides a composite intervertebral spacer including a body of bone having a surface-exposed irregularity and a complementary space-filling member fitted in the irregularity to provide a substantially uniform exterior surface to the spacer. Referring to FIGS. 14–15A, an elongated body of bone 70 having a surface-exposed irregularity such as an open channel 71 is shown. Channel 71 is preferably formed at least partially from a natural channel such as an inter-medullary canal. Wall 76 defines channel 71. At least two opposing arms 73 and 74 are connected to body 70. Opposing arms 73 and 74 define a mouth 75 to channel 71. In many instances, however, it will be desired that outer surface 72 of body 70 have a substantially uniform circumference. Moreover, preferred spacers often have an intact thru-hole bounded on all sides to assist in retaining an osteogenic material, e.g., a BMP-soaked collagen sponge, in the spacer during the insertion process and thereafter. For these reasons in accordance with the invention, a complementary member 80 as depicted in FIGS. 15 and 15A is disposed in the channel 71 of the body 70.

Complementary member 80 has an outer surface 81, a first end 82, a second end 83, a top surface 84 and a bottom surface 85. Referring now to FIGS. 14–17 together, the member 80 is complementary to body 70 in the sense that member 80, when fitted in channel 71, provides a uniform exterior surface to the overall spacer. In the illustrated case, the spacer has a cylindrical exterior surface, and thus viewed from a first axis "X", the top surface 84 and end surfaces 82 and 83 are, taken together, configured as an arc having the same radius "r" of that of bone body 70. In other words, the top surface 84 and end surfaces 82 and 83 together define an arc having a radius equal to that r' of the circumferential surface of body 70. Viewed from a second axis "Y" perpendicular to axis "X", member 80 has a surface defining an arc having a radius equal to that defined by surface 76 of channel 71. Space-filling member 80 may be comprised of a metal, metal alloy, ceramic, bone cement, polymer or any other material. However, space-filling member 80 is preferably comprised of bone and most preferably comprised of cortical bone. Space-filling member 80 may be obtained, for example, by taking a transverse plug from a long bone source. Space-filling member 80 is advantageously configured by methods known in the art, including machining, so as to close mouth 75 of channel 71 when inserted into the channel and provide a spacer including body 70 and member 80 to have a substantially uniform circumference. This can be accomplished by machining, sanding or otherwise configuring a cylindrical plug sized to fit snugly in channel 71. Such machining, sanding or other configuring can occur before insertion of the member 80 in channel 71, after such insertion, or both.

Figure 18:
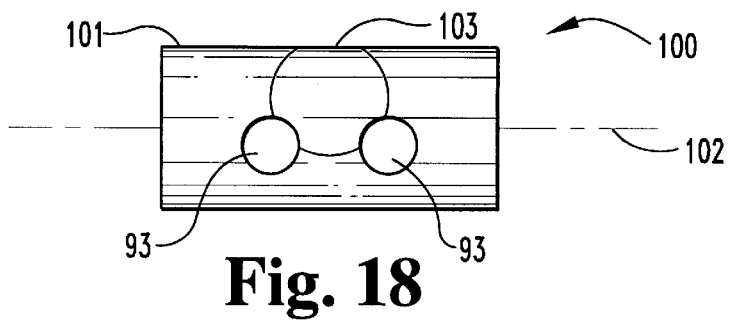
FIG. 18 is a side view of the intervertebral spacer depicted in FIGS. 16 and 17 with thru-holes.

In yet another embodiment depicted in FIG. 18, thru-holes 93 may be provided through body 101 of spacer 100. Although two thru-holes 93 are shown, one or several may be provided. As depicted in FIG. 18, thru-holes 93 extend transversely, e.g., perpendicularly, to longitudinal axis 102 of spacer 100. Moreover, thru-holes 93 may individually extend through body 101, space-filling member 103 or through both body 101 and space-filling member 103. Thru-holes 93 may be filled with an osteogenic material as described above to promote intervertebral fusion once the spacers are placed in the intervertebral space. These spacers may also be configured to have the surface features described above, including grooves, threads and/or an instrument attachment hole defined by a tool engaging end.

The body of the spacer above having a wall defining a C-shaped channel may be obtained by taking an off-center transverse plug from the diaphysis of a long bone. Preferably, the body is obtained using a diamond or hard metal tipped cutting bit which is water cleaned and cooled. Commercially available generally circular bits having an internal vacant diameter between about 10 mm to about 20 mm are preferred to obtain the body of the spacer. Such bits, and core drills for their use, are available, for example, from Starlite, Inc.

In one embodiment, a pneumatic driven miniature lathe having a spring loaded carriage which travels parallel to the cutter is used. The lathe has a drive system which is a pneumatic motor with a valve controller which allows a desired RPM to be set. The carriage rides on two runners which are 1.0 inch stainless rods and has travel distance of approximately 8.0 inches. One runner has set pinholes on the running rod which will stop the carriage from moving when the set pin is placed into the desired hole. The carriage is moveable from side to side with a knob which has graduations for positioning the graft. A vice on the carriage clamps the graft and holds it in place while the body or reinforcing member is being cut. The vice has a cut-out area in the jaws to allow clearance for the cutter.

Figure 19:
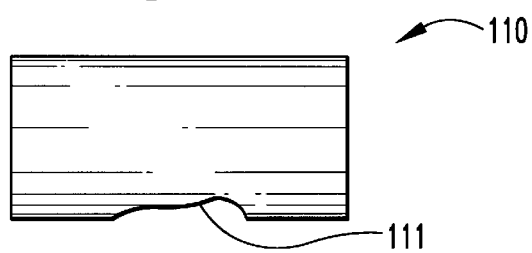
FIG. 19 is a side view of an alternative embodiment of a body component of the intervertebral spacer of the present invention.
Figure 20:
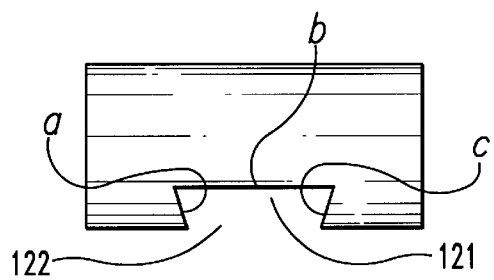
FIG. 20 shows the body of FIG. 19 with a shaped channel.
Figure 21:
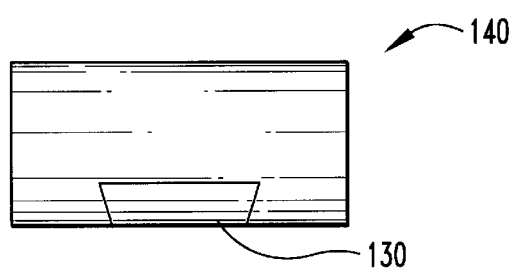
FIG. 21 shows an alternative embodiment of the intervertebral spacer of the present invention, including a complementary space-filling member disposed in the channel of the body depicted in FIG. 20.
Figure 22:
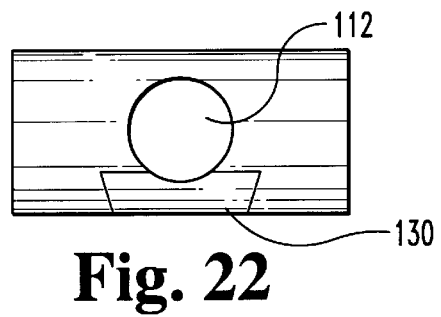
FIG. 22 shows the intervertebral spacer of FIG. 21 with a thru-hole.

In operation, the carriage is manually pulled back and locked in place with a set pin. The graft is loaded into the vice and is aligned with the cutter. Sterile water is used to cool and remove debris from the body, reinforcing member or space-filling member spacer component as it is being cut. The water travels down through the center of the cutter to irrigate as well as clean the spacer component under pressure. After the spacer component is cut, sterile water is used to eject it out of the cutter. The spacer component may be further prepared to enlarge or shape the channel as required by the circumstances, including reaming or machining the channel to a substantially circular or other shape. For example, FIG. 19 depicts body 110 having natural channel 111. The channel may be shaped to include a dovetail as depicted in FIG. 20. A complementary dovetail space-filling member 130 may be disposed in channel 122 to form spacer 140 depicted in FIG. 21. A thru-hole 112 may also be provided in spacer 140 as seen in FIG. 22. The device may be threaded after drilling the thru-hole as described above. Moreover, the complementary space filling member 130 is preferably held in place by 3 point contact. For example, complementary space-filling member is held in place by contacting surfaces a, b and c of channel 121. After machining, a form of terminal sterilization as known in the art may be performed to ensure sterility, including gamma or E-beam irradiation.

Spacer components of any size can be prepared according to this invention. In some embodiments, the bodies range from 5 mm to 30 mm diameters with lengths of about 8 mm to about 36 mm being generally acceptable, although other appropriate gradations in length and diameter are available. For bodies used as spacers for cervical fusion procedures, such as anterior cervical fusion (ACF) spacers, lengths of 8 mm, 9 mm, up to about 15 mm are generally desirable.

Bodies of differing diameter are most conveniently obtained as follows:

| Diameter | Source |
|---|---|
| 10.6–11 mm | fibula |
| 12 mm | radius |
| 14 mm | ulna |
| 14 mm | small humeri |

Bodies forming spacers for thoracic and lumbar fusions, such as anterior thoracic inner body fusion (ATIF) and anterior lumbar inner body fusion (ALIF), respectively, having a depth of between about 10–36 mm, and preferably between about 15–24 mm, are generally acceptable, depending on the needs of a particular patient. Spacers having bodies of differing diameter for thoracic and lumbar fusions are most conveniently obtained as follows:

| Diameter | Source |
|---|---|
| 14–16 mm | humerus |
| 16–18 mm | femur |
| 18–20 mm | tibia |

The present invention also provides a method of preparing an intervertebral spacer. In one aspect of the invention, the method includes providing a body of bone and a reinforcing member as shown and discussed with reference to FIGS. 1–5. The reinforcing member is typically configured to be received in the channel of the body. The method includes inserting the reinforcing member as described above into the channel. The method further may comprise including one or more thru-holes through the body to form a spacer as shown and discussed with respect to FIG. 3. The thru-hole(s) may be included in the body prior to or after insertion of the reinforcing member into the channel of the body and typically extends transverse to the longitudinal axis of the body. The thru-hole(s) may be filled with an osteogenic material as described above. Moreover, surface features such as grooves and/or threads may be included on the outer surface of the spacer after the thru-hole(s) is formed.

In another aspect of the invention, the method includes providing a body of bone as shown and discussed with reference to FIGS. 14–22 as well as a space-filling member as shown and discussed with reference to FIGS. 15, 15A, 16, 17, 21 and 22. The space-filling member is preferably configured to be received in the channel of the body of bone. The method includes inserting the space-filling member into the channel of the body of bone. The method may further comprise including at least one thru-hole through the body prior to inserting the space-filling member into the channel. The method may also comprise including a thru-hole through the body and space-filling member. The thru-hole typically extends transversely to the longitudinal axis of the body. In other embodiments of the invention, a second spacer may be implanted into the intervertebral space. When two spacers are implanted, they may positioned as known in the art. For example, the spacers may be positioned bilaterally.

The present invention also provides a method of fusing adjacent vertebrae. The spine may be approached from any direction indicated by the circumstances. The vertebrae and the intervertebral space are prepared according to conventional procedures to receive the intervertebral spacer. A spacer of the appropriate dimensions as described in FIGS. 1–22 is selected by the surgeon, based on the size of the cavity created and the needs of the particular patient. The spacer is then inserted into the cavity created between the adjacent vertebrae. Spacers with thru-holes may be filled with an osteogenic material described above prior to placing the spacer into the intervertebral space.

Spacers of the invention may also be perforated, for example by laser perforation generally as described by Lewandrowski et al., *Journal of Orthopaedic Research*, Vol. 15, No. 5 (1997). Preferred perforations will provide multiple holes with diameters less than about 1 mm extending through the spacers. Perforation, in accordance with the invention, may be used to facilitate more complete and uniform diffusion of agents into and through the spacers in pretreatments (for example in a pretreatment with a solution of bone morphogenetic protein or other active agent), and/or to facilitate fusion and resorption of the spacer.

Although the foregoing description discloses specific aspects of the present invention, those skilled in the art will recognize that any of a number of variations of the invention disclosed herein can be made. For example, it is contemplated that the spacers may have any shape that is amenable for proper fusion of adjacent vertebrae to occur, including polyhedral shapes. In addition, any of a number of known bone treatments can be applied to the spacer of this invention to alter its properties. For example, the methods disclosed in U.S. Pat. Nos. 4,627,853, 5,053,049, 5,306,303 and 5,171,279 can be adapted and applied to the invention disclosed herein. Accordingly, the disclosures of those patents are herein incorporated by reference for this purpose.

What is claimed is:

1. A composite intervertebral spacer, comprising:
   a) an elongate body of bone having a longitudinal axis and a channel extending perpendicular to said longitudinal axis, said channel formed at least partially from a natural channel;
   b) at least two opposing arms connected to said body, said opposing arms defining a mouth to said channel; and
   c) a space-filing member disposed within said channel, said composite spacer having a substantially uniform circumference.

2. The intervertebral spacer of claim 1, wherein said space-filling member is a bone plug.

3. The intervertebral spacer of claim 1, wherein said channel is shaped by reaming.

4. The intervertebral spacer of claim 1, further comprising a tool engaging end defining an instrument attachment hole.

5. The intervertebral spacer of claim 1, wherein said body of bone is obtained from an off-center transverse cut of the diaphysis of a long bone having an inter-medullary canal.

6. The intervertebral spacer of claim 2, wherein said bone plug comprises cortical bone.

7. An intervertebral spacer, comprising:
   a) an elongated body, said body having a wall defining a C-shaped chamber; and
   b) a space-filling member disposed within said chamber, said spacer having a substantially uniform circumference.

8. An intervertebral spacer, comprising:
   a) a body of bone having a longitudinal axis, a channel extending perpendicular to said longitudinal axis, said channel formed at least partially from an inter-medullary canal, a thru-hole extending through said spacer and transverse to said longitudinal axis;

b) at least two opposing arms connected to said body, said opposing arms defining a mouth to said channel; and c) a space-filling member disposed within said channel, said spacer having a substantially uniform circumference.

9. A method of preparing an intervertebral spacer, comprising:

providing an elongated body of bone having a longitudinal axis and a channel extending perpendicular to said longitudinal axis, said channel formed at least partially from a natural channel, at least two opposing arms connected to said body, said opposing arms defining a mouth to said channel;

providing a space-filling member configured to be received in said channel; and inserting said space-filling member into said channel to form said spacer, said spacer having a substantially uniform circumference.

10. The method of claim 9, further comprising forming a thru-hole through said body after inserting said space-filling member into said channel, said thru-hole extending transverse to said longitudinal axis.

11. The method of claim 9, wherein said body of bone is a transverse plug of a long bone having a medullary canal.

12. The method of claim 10, wherein said thru-hole extends through said body and said space-filling member.

13. A method of fusing adjacent vertebrae, comprising:

1) providing an intervertebral spacer including:

a) an elongated body of bone having a longitudinal axis and a channel extending perpendicular to said longitudinal axis, said channel formed at least partially from a natural channel;

b) at least two opposing arms connected to said body, said opposing arms defining a mouth to said channel;

c) a space-filling member disposed in said channel, said spacer having a substantially uniform circumference;

2) preparing adjacent vertebrae to receive the spacer in an intervertebral space between adjacent vertebrae; and 3) placing the spacer into the intervertebral space after said preparing step.

14. The method of claim 13, further comprising including at least one thru-hole through said body prior to inserting said space-filling member into said channel, said thru-hole extending transverse to said longitudinal axis.

15. The method of claim 13, wherein said space-filling member comprises cortical bone.

16. The method of claim 15, wherein said spacer includes at least one thru-hole through said body and said space-filling member, said thru-hole extending transverse to said longitudinal axis.

17. The method of claim 16, wherein said thru-hole is filled with an osteogenic material.

* * * * *